United States Patent [19]

Tarman et al.

[11] 4,289,625
[45] Sep. 15, 1981

[54] HYBRID BIO-THERMAL GASIFICATION

[75] Inventors: Paul B. Tarman, Elmhurst; David P. Chynoweth, St. Charles, both of Ill.

[73] Assignee: Institute of Gas Technology, Chicago, Ill.

[21] Appl. No.: 113,242

[22] Filed: Jan. 18, 1980

[51] Int. Cl.³ .............................................. C02F 3/28
[52] U.S. Cl. ................................... 210/603; 210/613; 210/770; 210/774
[58] Field of Search ........................................ 210/3–6, 210/8–10, 12, 16, 67, 71, 194, 68, 603, 604, 609, 613, 630, 768–771, 774

[56] References Cited

U.S. PATENT DOCUMENTS

| | | | |
|---|---|---|---|
| 2,097,454 | 11/1937 | Fischer | 210/9 X |
| 2,638,444 | 5/1953 | Kappe | 210/3 X |
| 3,345,288 | 10/1967 | Sontheimer | 210/10 |
| 3,383,309 | 5/1968 | Chandler | 210/3 X |
| 3,741,890 | 6/1973 | Smith et al. | 210/71 X |
| 4,076,515 | 2/1978 | Richard | 210/9 X |
| 4,190,528 | 2/1980 | Dassen | 210/12 X |
| 4,204,842 | 5/1980 | Morel et al. | 210/603 X |

Primary Examiner—Thomas G. Wyse
Attorney, Agent, or Firm—Thomas W. Speckman

[57] ABSTRACT

A hybrid bio-thermal gasification process for improved carbonaceous gasification wherein a biological feed is anaerobically digested with product methane and carbon dioxide containing gas withdrawn from the digester and biological residue separately withdrawn from the digester and introduced into a thermal gasifier wherein at least a substantial portion of the biological residue is gasified under elevated temperature conditions producing thermal gasifier products and thermal residue with at least a portion of the thermal gasifier products or their derivatives being returned to the digester. The process provides high conversion of the carbonaceous material and biological feed stocks to gas products and permits gasification of a wider variety of biological feeds by anaerobic digestion processes while requiring less external nutrient feeding to the process. The process of this invention provides a highly efficient process for production of substitute natural gas. Various advantages of interrelation between the anaerobic digester and thermal gasification are taught.

28 Claims, 3 Drawing Figures

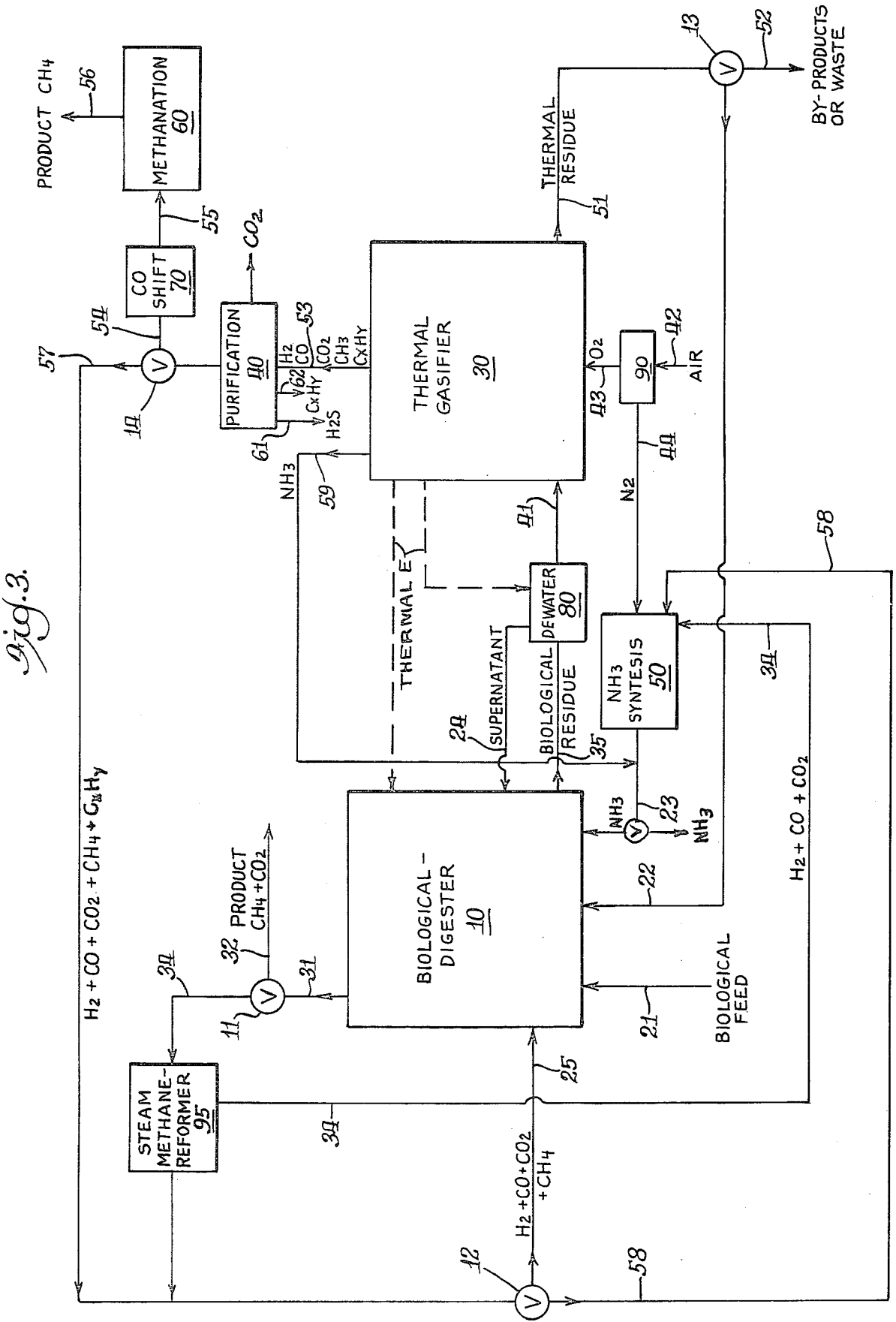

HYBRID BIO-THERMAL GASIFICATION

BACKGROUND OF THE INVENTION

1. Field of the Invention

Methane production by anaerobic digestion has been widely practiced, particularly with respect to digestion of sewage sludge organic waste. In recent times, the worldwide energy shortage has furthered consideration and improvement of non-fossil sources of energy. Biological materials, including organic wastes, represent a large renewable potential energy resource. This invention relates to improved gasification from biological materials by hybrid biological-thermal gasification to provide substantially increased conversion of the organic component of the biological feed material, including terrestrial and aquatic energy crops, organic wastes and peat. The process of this invention provides anaerobic digestion of a biological feed producing methane containing gas followed by thermal gasification of the biological residue from the anaerobic digestion, the thermal gasification providing product gas for supply to the anaerobic digester for production of methane. The thermal residue from such gasification may be recycled to the anaerobic digester to provide phosphorus and other inorganic nutrients. The hybrid bio-thermal gasification process of this invention broadens the range of biological feeds suitable for conversion, provides higher gas and methane production per pound of biological feed, and substantially reduces the quantity of residue from the process. The hybrid bio-thermal gasification process of this invention may provide medium Btu fuel gas, substitute natural gas (SNG) and hydrogen containing gas for a variety of uses.

2. Description of the Prior Art

The production of methane gas by anaerobic digestion of various organic wastes has been known. There have been continuous efforts to improve methane yield resulting from anaerobic digestion. Most of the prior attempts to increase methane yield have been centered around anaerobic digestion as practiced in municipal waste treatment plants as exemplified by U.S. Pat. Nos. 3,640,846, teaching addition of coal; 3,981,800, teaching pressurized digestion; and 4,022,665, teaching two phase digestion of sewage sludge. Other attempts to improve the production rate and yield of methane by anaerobic digestion have related to improved anaerobic digestion by utilization of liberated enzymes of the biomass for contribution to more efficient digestion as taught by U.S. Pat. No. 3,994,780.

U.S. Pat. No. 2,638,444 and U.S. Pat. No. 4,100,023 teach recycling product gases from an anaerobic digester back to the digester for the function of agitation and heat addition. However, such gases would principally contain methane and carbon dioxide which may inhibit methane production due to mass action. The shift conversion of carbon monoxide and water to carbon dioxide and hydrogen and the anaerobic production of methane from carbon monoxide, carbon dioxide and hydrogen has been reported by D. L. Wise, C. L. Cooney and D. C. Augenstein, *Biomethanation: Anaerobic Fermentation of $CO_2$, $H_2$, and CO to Methane*, Biotechnology and Bioengineering, Vol. XX, Pp. 1153–1172 (1978). The biological conversion of carbon monoxide to methane has also been reported in *Pure Cultures of Methanogenic Bacteria* by Daniels and Zeikus, Journal of Bacteriology, 136; 75 (1977).

The prior art, while recognizing the desirability to increase methane production resulting from anaerobic digestion, does not suggest the combination of biological and thermal gasification to utilize substantially all of the organic hydrocarbon material in the biological feed.

SUMMARY OF THE INVENTION

The process of this invention provides a hybrid biological-thermal process for improved hydrocarbon gasification comprising adding biological feed to an anaerobic digester, anaerobically digesting the biological feed under thermophilic or mesophilic conditions in an active liquid culture, introducing a gasification product to the active liquid culture during the anaerobic digestion, withdrawing product methane and carbon dioxide gas from the digester and separately withdrawing biological residue from the digester and introducing it into a thermal gasifier wherein the biological residue is gasified under elevated temperature conditions thereby producing thermal gasifier products and thermal residue with at least a portion of the thermal gasifier products or their derivatives being passed through the anaerobic digester. In one embodiment, at least a portion of the thermal residue is returned to the biological digester to provide inorganic nutrients for the anaerobic digestion. In another embodiment, ammonia is added to the anaerobic digester, the ammonia being a thermal gasifier product or produced from product gases of the thermal gasifier and biological digester. The process of this invention provides for the biomethanation of carbon monoxide and/or hydrogen and/or carbon dioxide produced by thermal gasification of the biological residue from the biological digester providing higher methane production per unit of feed than conventional digestion process. In another embodiment, the methane and carbon dioxide product of the digester may be reformed to hydrogen, carbon monoxide and carbon dioxide for recycle to the digester to increase the rate of digestion.

It is an object of this invention to provide a process for high conversion of carbonaceous material in biological feed stocks to gas products thereby greatly reducing waste disposal problems associated with conventional anaerobic digestion processes.

It is another object of this invention to provide a gasification process applicable to a wider variety of biological feed stocks than presently available anaerobic digestion processes.

It is a further object of this invention to provide a combined biological anaerobic digestion and thermal gasification process for high efficiency production of methane containing gases.

It is still another object of this invention to provide a hybrid biological-thermal process for methane production which efficiently converts feed stocks having high water content, greater than 50 percent.

It is yet another object of this invention to provide a hybrid biological-thermal carbonaceous gasification process requiring less external nutrient feeding by nutrient recycle of thermal residue to the anaerobic digester.

It is a further object of this invention to provide a carbonaceous gasification process having high thermal efficiency.

BRIEF DESCRIPTION OF THE DRAWINGS

Other objects and advantages of this invention will be apparent by reading of the further description of the preferred embodiments and by reference to the drawings setting forth preferred embodiments wherein:

FIG. 3 is a schematic process flow diagram showing another preferred embodiment of this invention.

DESCRIPTION OF PREFERRED EMBODIMENTS

Figure 1:
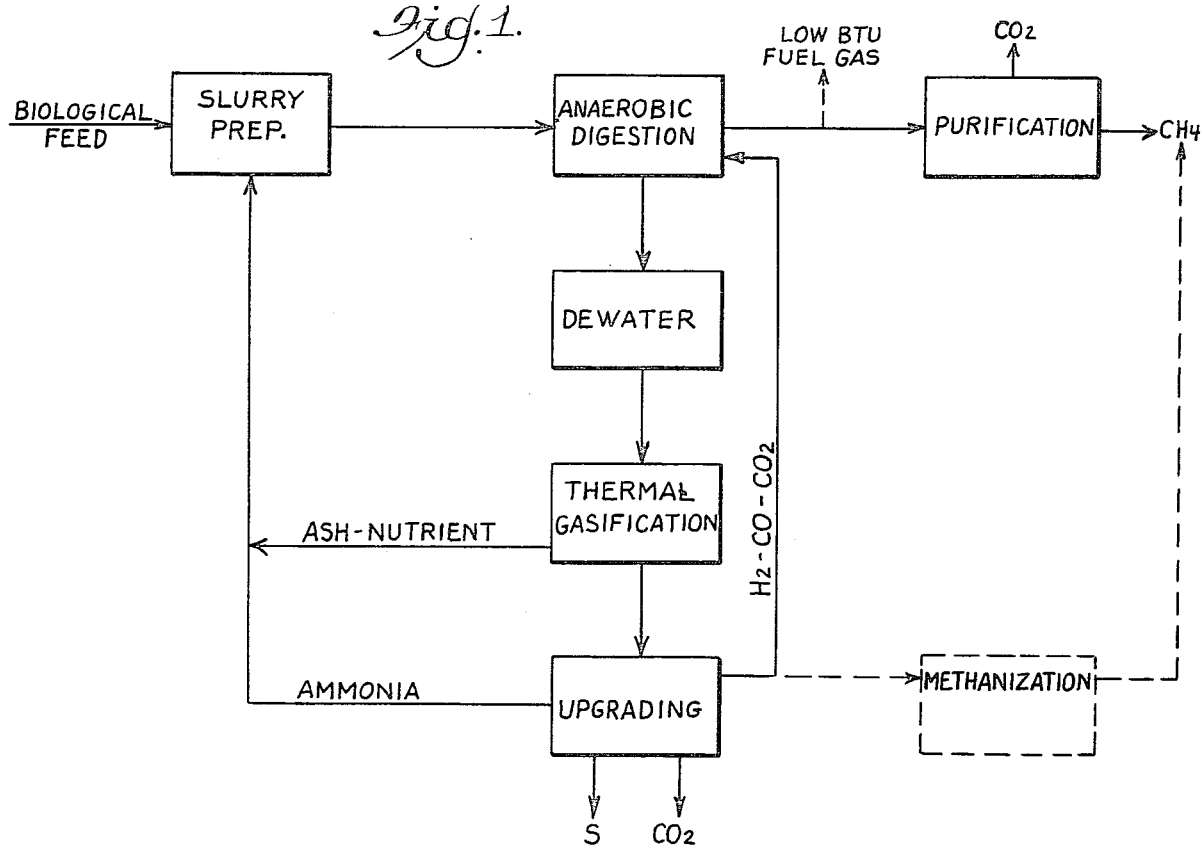
FIG. 1 is a simplified schematic diagram showing the relationship of basic steps of the process of this invention.

The term "biological feed" as used in this description and the appended claims includes plant material which may be of terrestrial or aquatic origin, peat and organic waste which includes all types of organic refuse including sewage sludge, animal waste, municipal waste, industrial waste, forestry waste, agricultural waste, and the like. The term "carbonaceous" includes biological feeds, biological digester residue and thermal gasification residue.

Plant material may include any of the organisms of the kingdom of Plantae which typically have cell walls composed of cellulose in large part and have nutritive systems in which carbohydrates are formed photosynthetically. The plant material useful in this invention is fresh harvested or stored plant material, which is usually grown on farms for this purpose, and is untreated chemically or physically, except for size reduction. Terrestrial plants include warm season grasses, such as Bermuda grass and Elephant grass; cool season grasses, such as Kentucky Blue grass and Merion Blue grass; reedy plants, such as Bamboo, rice, cattails; herbaceous plants, such as Kudzu and maze; deciduous trees, such as eucalyptus and poplar; and coniferous trees, such as white and red pines. Exemplary aquatic plants include water hyacinth, duck weed, algae, sea kelp and sargassum.

The suitability of organic waste such as sewage sludge, animal waste, municipal waste and industrial waste for anaerobic digestion is well known in the art. Treatment of municipal solid waste and industrial solid waste for removal of undesired material such as glass, metals, plastics, stones, and the like, is well known to the art. Forestry waste and agricultural waste includes portions of plants after some physical or chemical treatment, usually not including the entire plant, for example, stumps from logging, sawdust, wood chips, corn stalks, corncob and bagasse.

The anaerobic digestion of biological feed according to this invention may be carried out under conditions of temperature, both mesophilic (about 20° to 45° C.) and thermophilic (about 45° to 70° C.); retention times in excess of about 3 days and usually about 5 to 30 days, preferably about 8 to 16 days; loading rates; pretreatment of feed; digester mixing and recycling as known to the art for anaerobic digestion and pointed out more particularly in the references identified above. The present invention may be readily applied to multi-stage digestion, such as exemplified by U.S. Pat. No. 4,022,665. Shorter retention times than set forth above may be used in the present invention under conditions where digestion is accelerated by the process.

Any active methane producing mesophilic or thermophilic anaerobic digestion system may be used. Methane-producing anaerobic systems utilizing acid forming bacteria and methane-producing organisms as well known to be employed to produce methane from sewage sludge can be employed in practice of the present invention.

A review of the microbiology of anaerobic digestion is set forth in Biogenesis of Methane, R. A. Mah, D. M. Ward, L. Baresi and T. L. Glass, Ann. Rev. Microbiol. 31, pgs. 309-341 (1977), the contents of which is incorporated in its entirety herein by reference. It is usually preferred to use mixed cultures to obtain the most complete fermentation action. Nutritional balance and pH adjustments may be made to the digester system as is known to the art to optimize methane production from the culture used.

Referring to the figures, the biological feed may be ground and mixed with water and nutrients derived primarily from process streams prior to introduction into biological digester 10. The biological feed may be deficient in inorganic and organic nutrients which may be added to the biological digester or to the feed and derived from the thermal residue, the thermal gasification products and dewatering, thus substantially broadening the suitable biological feeds. Inorganic nutrients, such as phosphorus, are derived principally from thermal residue and ammonia may be derived by recovery from gases produced by thermal gasification. Liquids and nutrients may be derived from dewatering of biological residue of the anaerobic digester and recycled to the digester. Thus, the process may be readily adjusted with respect to nutrients and chemical deficiencies of biological feeds by internal adjustments thereby alleviating the requirement of addition of chemicals to the overall process, especially on a continual basis during digestion.

The water content of the biological feed is not important and may be high, more than 50 weight percent. One of the features contributing to the high overall energy efficiency of this process is the availability of thermal energy used in thermal gasification for heating the anaerobic digester and to facilitate dewatering prior to thermal gasification.

As previously disclosed, biological digester 10 may be of any configuration suitable for anaerobic production of methane containing gas and may comprise multiple stage digesters with the supernatant from a sedimentation stage being recycled to the biological feed preparation means. As shown in the figures, gasification products from the thermal gasifier which may contain hydrogen, carbon dioxide, and carbon monoxide may be provided to biological digester 10 from thermal gasifier 30 and, if desired, from conversion of product gas of biological digester 10 by steam-methane reformer 95 as shown in FIG. 3.

Figure 2:
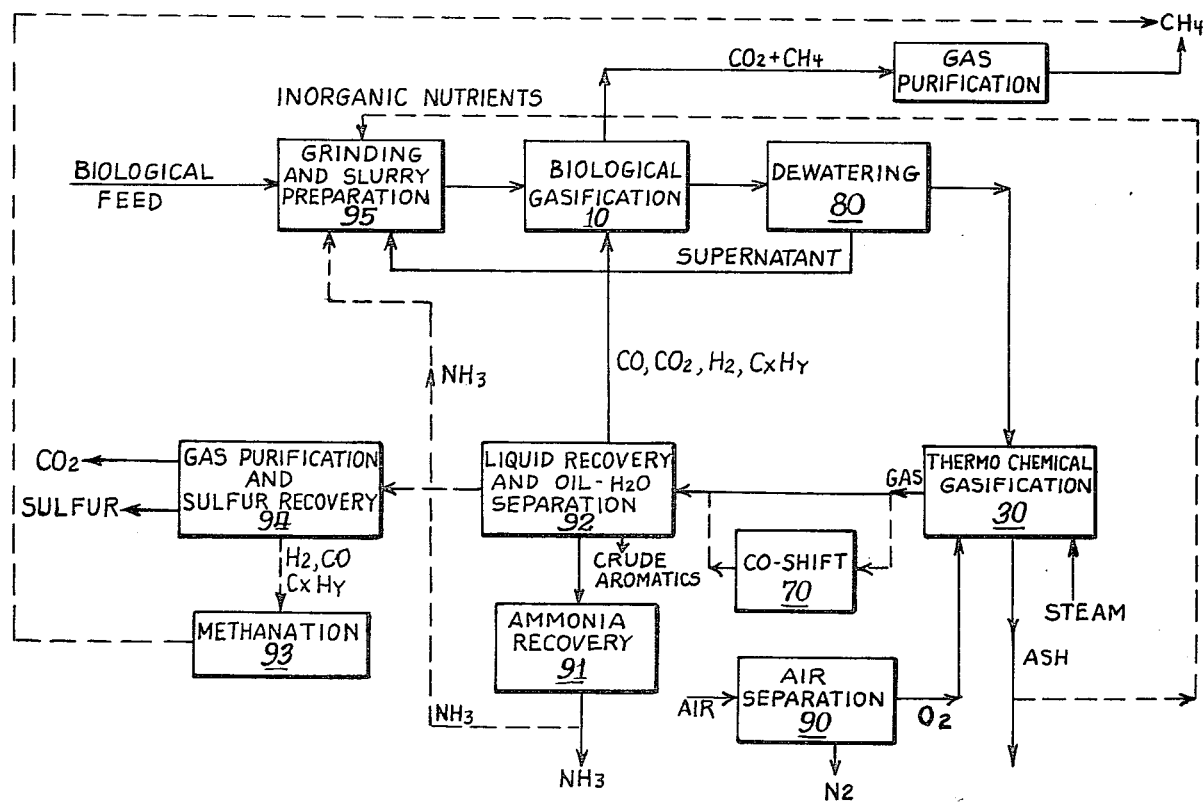
FIG. 2 is a schematic process flow diagram showing one preferred embodiment of this invention.

Ammonia for anaerobic digestion may be derived directly from products of thermal gasifier 30 by ammonia recovery means 91 shown in FIG. 2 and may be added to biological digester 10 or slurry preparation means 95. When excess ammonia is available from the gasifier products, it may be withdrawn from the process as shown in FIG. 2. When insufficient ammonia is available from gasifier products, it may be synthesized as shown in FIG. 3 by ammonia synthesis means 50 using nitrogen from air separation means 90, and product gases from thermal gasifier 30 and/or product gases from biological digester 10. The product gases from biological digester may be passed through steam-methane reformer means 95 and the product passed to ammonia synthesis means 50.

Product methane containing gas, from biological digester 10, principally methane and carbon dioxide, may be used directly as medium Btu fuel gas as shown in FIG. 3 or may be purified and upgraded by methods known to the art to provide substitute natural gas (SNG).

At least a portion of produced gases from thermal gasifier 30 may be fed to biological digester 10 or ammonia synthesis means 50 or may be withdrawn from the process system for use as fuel gas. It is desirable to remove deleterious aromatics or higher hydrocarbons and sulfur containing compounds from such product gases as shown by liquid recovery means 92 and purification means 94 in FIG. 2 and purification means 40 in FIG. 3. Such purified gases may be subject to carbon monoxide shift reactions in shift means 70, shown in FIG. 3, and upgraded by methanation means 60 to result in product gas having high methane content and qualities of substitute natural gas (SNG).

Biological residues from biological digester 10 are preferably dewatered to a water content of less than about 75–80 weight percent, preferably less than about 50 weight percent and transferred to thermal gasifier 30. The supernatant from the dewatering process may be used as biological feed slurry dilution as needed.

Thermal gasifier 30 is operated under elevated temperature conditions to gasify a substantial portion of the biological residues, usually at temperatures of about 1200° to about 1800° F. Thermal energy for the thermal gasifier may be obtained by utilization of a portion of the product gases of the biological digester and/or product gases of the thermal gasifier. The thermal gasification may be carried out in a single or multiple stage gasifier under conditions of pressure and residence time to gasify a substantial portion of the carbonaceous material in the biological residue, greater than 50 weight percent and preferably greater than 75 weight percent. It is preferred that the thermal gasifier be operated under pressures from atmospheric up to about 1000 psig. Moving bed or fluidized bed gasifiers are also suitable as will be apparent to those skilled in the art. Generally, residence times in the thermal gasifier in the order of about 3 to 60 minutes are suitable. The thermal residue from thermal gasifier 30 represents a substantially lessened disposal problem than does the biological residue from biological digester 10 which has created disposal problems with prior processes. Suitable thermal gasifiers include those such as described in the publication Status of the Peat Gas Process, D. Punwani, paper at Tenth Synthetic Pipeline Gas Symposium, Chicago, Ill., October. 1979, and in the publication U-GAS TECHNICAL STATUS, J. G. Patel, Symposium on Advances in Coal Utilization Technology, Louisville, Ky., May, 1979, which are incorporated herein by reference in their entireties.

The remainder of the auxiliary processes referred to in FIGS. 2 and 3 are known to the art. For example, methanation and CO shift processes suitable include multi-fixed bed processes with gas recycle as described and sold by C. F. Braun. Suitable purification and carbon dioxide and sulfur recovery include acid gas removal processes as described in Gas Purification, Arthur Kohl and Fred Riesenfeld, second edition (1974). Suitable steam-methane reforming include well known Girdler processes. Air separation processes operating at low temperatures are suitable, such as Linde processes. Dewatering may be accomplished by filter presses of fixed bed roller processes as known in the art. Ammonia synthesis may be performed by known processes, such as Kellogg ammonia synthesis processes.

The valves shown in FIG. 3 may divert the process stream to any or all of the pathways shown in the figure.

The thermal energy transfer from thermal gasifier 30 to biological digester 10 and to dewatering means 80 may be by any heat exchanger means known to the art. Details and materials of construction for use in the process of this invention will be apparent to those skilled in the art.

EXAMPLE I

Digester feed for anaerobic digestion of 24 weight percent on total solids basis of activated sewage sludge and 76 weight percent on total solids basis primary sludge was fed to an active culture volume of 1.5 l at a rate of 1 l/day with wasting at 1/l/day. The digester was maintained under anaerobic digestion conditions at about 35° C. The sludge mixture had a total solids content of 5.35 weight percent of slurry and volatile solids content of 67.37 weight percent of total solids and an elemental analysis as follows:

| Elements | Sludge - Wt. % Dry |
|---|---|
| Carbon | 38.7 |
| Hydrogen | 5.46 |
| Nitrogen | 4.35 |
| Phosphorus | 1.40 |
| Sulphur | 0.77 |
| Heating value Btu/dry lb. | 7128 |

The organic loading of the digester was 0.15 lb.VS/ft$^3$-day and retention time 15 days. At steady state conditions, the digester was found to produce methane at the rate of 1.134 Std. l/day (60° F., 30" Hg.). The digester effluent or biological residue quality was as set forth in Table I.

EXAMPLE II

The same digester system as set forth in Example I was operated with a continuous purge to the lower portion of the active liquid culture of 30 percent hydrogen, 40 percent carbon dioxide and 30 percent carbon monoxide (all on a mole-percent basis) at a flow rate of 57 Std. l/day. Total methane production was 2.472 Std. l/day, 1.162 from biological feed and 1.310 from gaseous feed. The digester effluent or biological residue quality was as set forth in Table I.

EXAMPLE III

The same digester system as set forth in Example I was operated with a continuous purge to the lower portion of the active liquid culture of 30 percent hydrogen, 40 percent carbon dioxide and 30 percent helium (all on a mole-percent basis) at a flow rate of 61 Std. l/day. Total methane production was 2.926 Std. l/day, 1.181 from biological feed and 1.745 from gaseous feed. The digester effluent or biological residue quality was as set forth in Table I.

EXAMPLE IV

The same digester system as set forth in Example I was operated with a continuous purge to the lower portion of the active liquid culture of 40 percent carbon dioxide, 30 percent carbon monoxide and 30 percent helium (all on a mole-percent basis) at a flow rate of 50 Std. l/day. Total methane production was 1.676 Std. l/day, 1.191 from biological feed and 0.485 from gaseous feed. The digester effluent or biological residue quality was as set forth in Table I.

|  | Ex. I | Ex. II | Ex. III | Ex. IV |
|---|---|---|---|---|
|  | Digester Effluent Quality and Performance | | | |
| pH | 7.29 | 7.18 | 7.20 | 7.20 |
| Volatile Acids, mg/las Acetic | 56 | 20 | 12 | 26 |
| Total Alkalinity, ppm as $CaCO_3$ | 7920 | 7100 | 7070 | 7100 |
| $NH_3$—N, ppm asN | 1146 | 1245 | 1209 | 1185 |
| Total COD, mg/l | 17900 | 18750 | 19080 | 17320 |
| Density, gm/l | 1.022 | 1.019 | 1.019 | 1.020 |
| Total Solids, wt % of slurry | 3.59 | 3.42 | 3.40 | 3.33 |
| Volatile Solids, wt % of TS | 56.00 | 58.06 | 57.03 | 57.78 |
| Elements, Wt % of TS | | | | |
| Carbon | 31.70 | 32.25 | 32.10 | 32.40 |
| Hydrogen | 4.45 | 4.63 | 4.56 | 4.60 |
| Nitrogen | 3.96 | 4.21 | 4.14 | 4.19 |
| Sulfur | 1.13 | 0.98 | 0.99 | 1.07 |
| Phosphorus | 1.85 | 1.90 | 2.00 | 2.00 |
| Heating Value, Btu/dry lb. | 5823 | 6010 | 5943 | 5963 |
| Filtrate Volume, ml (60 sec. at 20″ Hg through an Eimio PO-808HF filter cloth) (N 30 ml) | 18 | 19 | 22 | 23 |

TABLE 1

|  | Ex. I | Ex. II | Ex. III | Ex. IV |
|---|---|---|---|---|
|  | Digestion and Purge Gas Conversion Efficiencies | | | |
| VS Reductions, % | | | | |
| $\frac{VS_{in} - VS_{out}}{VS_{in} - (VS_{in} \times VS_{out})}$ | 43.1 | 38.9 | 45.2 | 45.7 |
| $(VS_{feed} - VS_{effluent})/VS_{feed}$ | 38.4 | 33.0 | 35.7 | 33.7 |
| Carbon Recoveries in $CH_4$, % | | | | |
| feed solids | 27.8 | 28.5 | 29.0 | 29.2 |
| feed gas | — | 3.28 | 7.17 | 1.15 |
| Energy Recoveries in $CH_4$, % | | | | |
| from feed solids | 48.2 | 49.4 | 50.2 | 50.6 |
| from feed gas | — | 12.0 | 29.5 | 8.46 |
| $CH_4$ Yield from feed solids, SCF/lb. VS | 5.04 | 5.16 | 5.25 | 5.29 |
| Hydrogen Recoveries in $CH_4$, % | | | | |
| from feed solids | 66.3 | 67.9 | 69.0 | 69.6 |
| from feed gas | — | 15.3 | 19.0 | — |

EXAMPLE V

Bermuda grass biological feed is fed to a process as shown generally in FIG. 2 wherein the principal portion of the product gas of the thermal gasifier is subjected to chemical methanation results in cold gas efficiency of about 74%.

Bermuda grass having the following properties is ground and slurried for introduction to an anaerobic digester:

| Total Moisture, % total wt. | 33.0 |
|---|---|
| Total Solid, % total wt. | 67.0 |
| Volatile solids, % dry wt. | 95.0 |
| Ash, % dry | 5.05 |
| Heating Value, Btu/lb. dry | 8180 |
| Total Carbon, % | 47.1 |
| Total Hydrogen, % | 6.04 |
| Total Oxygen, % | 39.6 |
| Total Nitrogen, % | 1.96 |
| Total Sulfur % | 0.21 |

Anaerobic digestion is carried out under the following conditions:

| Temperature | 35° C. (95° F.) |
|---|---|
| Culture Volume | 126.7 × $10^6$ ft$^3$ |
| Loading | 0.15 lb VS/ft$^3$-day |
| Retention Time | 12 days |
| Methane Yield | 3.50 SCF/lb VS Added-day |
| Methane Content in Digester Gas | 60 mol % |

The biological residue is dewatered and fed to a steam-oxygen two stage thermal gasifier operated under the following conditions:

| Stage One | |
|---|---|
| Temperature | 1700° F. |
| Pressure | 545 psig |
| Solids Residence Time | 10 min. |
| Stage Two | |
| Temperature | 1475° F. |
| Pressure | 530 psig |
| Solids Residence Time | 1 second |

The product gases are subject to catalytic methanation at 830° F. and 410 psig resulting in gas having methane content of 94 mole percent.

The process using feed input of $163.7 \times 10^9$ Btu/day (10,000 Tons/day) will result in SNG $121.2 \times 10^9$ Btu/day (2595 TPD); ammonia $3.2 \times 10^9$ Btu/day (166 TPD) and organic and inorganic by-products $9.4 \times 10^9$ Btu/day (1320 TPD). The energy balance is as follows:

| Input, $10^9$ Btu/day | Output, $10^9$ Btu/day |
|---|---|
| A. Across Biological Gasification | |
| Bermuda Grass | Methane Gas 66.5 |

-continued

| Input, 10⁹ Btu/day | | Output, 10⁹ Btu/day | |
|---|---|---|---|
| as Feed | 163.7 | | |
| | | Total Solids | 92.9 |
| | | Heat Losses | 4.3 |
| | 163.7 | | 163.7 |
| B. Across Dewatering | | | |
| Total Solids | 92.9 | Methane Gas | 3.4 |
| | | Solids in Cake | 87.8 |
| | | Solids leaving with liquid streams | 0.8 |
| | | Losses | 0.9 |
| | 92.9 | | 92.9 |
| C. Across Thermal Gasification | | | |
| Solids to Gasifier | 68.5 | Pipeline Gas | 50.7 |
| | | By-Products | 12.6 |
| Solids to Steam and Power Generation | 19.3 | Losses | 23.0 |
| | | Motive Power | 1.5 |
| | 87.8 | | 87.8 |

EXAMPLE VI

Another process is conducted as described in Example V except that the thermal gasifier product gas is subjected to biological methanation by recycle to the anaerobic digester resulting in SNG 111.4×10⁹ Btu/day (2385 TPD) and a cold gas efficiency of 68%. The only changes in the energy balance are that item "C" is Across Thermal Gasification and Biomethanation with Methane Gas of 41.5×10⁹ Btu/day and Losses of 32.2×10⁹ Btu/day.

EXAMPLE VII

Biological feed of a blend of 90 wt. percent (dry basis) municipal solid waste and 10 wt. percent sludge is fed to a process as shown generally in FIG. 2 wherein the principal portion of the product gas of the thermal gasifier is subjected to biomethanation by recycle to the anaerobic digester which results in cold gas efficiency of about 60%.

The blend having the following properties is slurried for introduction to an anaerobic digester:

| | |
|---|---|
| Total Moisture, % total wt. | 31.13 |
| Total Solids, % total wt. | 68.87 |
| Volatile Solids, % dry wt. | 81.45 |
| Ash, % dry | 19.11 |
| Heating Value, Btu/lb dry | 7477 |
| Total Carbon, wt. % | 42.19 |
| Total Hydrogen, wt. % | 5.60 |
| Total Oxygen, wt. % | 31.88 |
| Total Nitrogen, wt. % | 1.22 |

Anaerobic digestion is carried out under the following conditions:

| | |
|---|---|
| Temperature | 35° C. |
| Culture Volume | 5.07 × 10⁶ ft³ |
| Loading | 0.20 lb VS/ft³-day |
| Retention Time | 15 days |
| Methane Yield | 3.5 SCF/lb VS added |
| Methane Content in Digester Gas | 60 mol % |

The biological residue is dewatered and fed to a steam-oxygen single stage thermal gasifier operated under the following conditions:

| | |
|---|---|
| Reactor Temperature | 1700° F. |
| Reactor Pressure | 350 psig |
| Carbon Conversion | 95% |

The product gases are passed to the anaerobic digester for biomethanation.

The process using feed input of 11.6×10⁹ Btu/day (778 Tons/day) will result in SNG 6.9×10⁹ Btu/day (149 TPD); and organic and inorganic by-products 1.4×10⁹ Btu/day (160 TPD). The energy balance is as follows:

| Input, 10⁹ Btu/day | | Output, 10⁹ Btu/day | |
|---|---|---|---|
| A. Across Biological Gasification | | | |
| Total Solids to Digester | 9.3 | Methane Gas | 3.6 |
| | | Solids in Effluent | 5.2 |
| | | Heat Losses | 0.5 |
| | 9.3 | | 9.3 |
| B. Across Dewatering | | | |
| Solids in Effluent | 5.2 | Solids in Cake | 5.1 |
| | | Solids leaving with liquid streams | 0.1 |
| | 5.2 | | 5.2 |
| C. Across Thermal Gasification | | | |
| Solids in Cake to Gasifier | 5.1 | Methane Gas | 3.4 |
| | | By-Products | 1.3 |
| Solids to Steam and Power Generation | 2.3 | Losses and Motive Power | 2.7 |
| | 7.4 | | 7.4 |

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A hybrid bio-thermal gasification process for improved carbonaceous gasification comprising: adding biological feed to an anaerobic digester; anaerobically digesting said biological feed under thermophilic or mesophilic conditions in an active liquid culture; introducing a gasification product to said active liquid culture during said anaerobic digesting; withdrawing product methane and carbon dioxide containing gas from said digester; separately withdrawing biological residue from said digester and introducing it into a thermal gasifier; gasifying at least a substantial portion of said biological residue under elevated temperature conditions producing thermal gasifier products and thermal residue, at least a portion of said thermal gasifier products or their derivatives being passed through said digester as said gasification product.

2. The process of claim 1 wherein said portion of thermal gasifier products is hydrogen containing gas at least a portion of which is converted to methane by said active culture.

3. The process of claim 1 wherein said portion of thermal gasifier products is carbon monoxide containing gas at least a portion of which is converted to methane by said active culture.

4. The process of claim 1 wherein said portion of thermal gasifier products is carbon dioxide containing gas at least a portion of which is converted to methane by said active culture.

5. The process of claim 1 wherein said portion of thermal gasifier product gas is methane containing gas.

6. The process of claim 1 wherein said portion of thermal gasifier products is ammonia.

7. The process of claim 1 wherein said portion of thermal gasifier products is gas comprising hydrogen, carbon monoxide and carbon dioxide.

8. The process of claim 1 wherein at least a portion of said thermal residue is added to said anaerobic digester to provide inorganic nutrients.

9. The process of claim 1 wherein said biological residue is dewatered to less than about 80 weight percent water prior to introduction to said thermal gasifier.

10. The process of claim 9 wherein at least a portion of the supernatant from said dewatering is recycled to said anaerobic digester.

11. The process of claim 9 wherein said biological residue is dewatered to less than about 50 weight percent water prior to introduction to said thermal gasifier.

12. The process of claim 11 wherein at least a portion of the supernatant from said dewatering is recycled to said anaerobic digester.

13. The process of claim 1 wherein at least a portion of said thermal gasifier products is gas used as a feed for ammonia synthesis to provide ammonia to said biological digester.

14. The process of claim 1 wherein at least a portion of said thermal gasifier products is gas fed to said biological digester.

15. The process of claim 1 wherein at least a portion of said product methane and carbon dioxide containing gas from said digester is withdrawn from the process for use in medium Btu fuel gas.

16. The process of claim 1 wherein at least a portion of said thermal gasifier products is hydrogen containing gas and is withdrawn from the process as hydrogen containing gas.

17. The process of claim 1 wherein at least a portion of said product methane and carbon dioxide containing gas from said digester is steam reformed to hydrogen, carbon monoxide and carbon dioxide and fed to said biological digester.

18. The process of claim 1 wherein at least a portion of said product methane and carbon dioxide from said anaerobic digester is additionally purified resulting in substitute natural gas (SNG).

19. The process of claim 18 wherein at least a portion of said thermal gasifier product gas is hydrogen, carbon monoxide and carbon dioxide containing gas and is additionally subject to a carbon monoxide shift reaction and methanation resulting in substitute natural gas (SNG).

20. The process of claim 1 wherein said biological feed comprises terrestrial plant material.

21. The process of claim 1 wherein said biological feed comprises aquatic plant material.

22. The process of claim 1 wherein said biological feed comprises organic waste.

23. The process of claim 1 wherein said biological feed comprises peat.

24. The process of claim 1 wherein said thermal gasifier is operated at temperatures of about 1200° to about 1800° F.

25. A hybrid bio-thermal gasification process for improved carbonaceous gasification comprising: adding biological feed to an anaerobic digester; anaerobically digesting said biological feed under thermophilic or mesophilic conditions in an active liquid culture; withdrawing product methane and carbon dioxide containing gas from said digester; separately withdrawing biological residue from said digester and introducing it into a thermal gasifier; gasifying at least a substantial portion of said biological residue under elevated temperature conditions producing thermal gasifier products and thermal residue, said thermal gasifier providing thermal energy to raise the temperature of said active liquid culture for improved methane production.

26. The process of claim 25 wherein said thermal gasifier is operated at temperatures of about 1200° to about 1800° F.

27. A hybrid bio-thermal gasification process for improved carbonaceous gasification comprising: adding biological feed to an anaerobic digester; anaerobically digesting said biological feed under thermophilic or mesophilic conditions in an active liquid culture; withdrawing product methane and carbon dioxide containing gas from said digester; separately withdrawing biological residue from said digester and introducing it into a thermal gasifier; gasifying at least a substantial portion of said biological residue under elevated temperature conditions producing thermal gasifier products and thermal residue, at least a portion of thermal energy from said thermal gasifier being used for dewatering said biological residue.

28. The process of claim 27 wherein said thermal gasifier is operated at temperatures of about 1200° to about 1800° F.

* * * * *